(12) United States Patent
    Walker (10) Patent No.: US 8,986,354 B2
(45) Date of Patent: Mar. 24, 2015

(54) SURGICAL KIT FOR SPINAL SURGERY

(75) Inventor: John Lawrence Walker, Madison, MS (US)

(73) Assignee: Zavation LLC, Brandon, MS (US)

( * ) Notice: Subject to any disclaimer, the term of this patent is extended or adjusted under 35 U.S.C. 154(b) by 150 days.

(21) Appl. No.: 13/396,045

(22) Filed: Feb. 14, 2012

(65) Prior Publication Data
US 2013/0211462 A1     Aug. 15, 2013

(51) Int. Cl.
*A61B 17/80*    (2006.01)
*A61B 17/58*    (2006.01)
*A61B 17/60*    (2006.01)
*A61F 2/00*     (2006.01)

(52) U.S. Cl.
USPC .............................. 606/289; 606/96; 606/295

(58) Field of Classification Search
USPC ............ 606/289, 290, 292, 293, 294, 295, 96
See application file for complete search history.

(56) References Cited

U.S. PATENT DOCUMENTS

| | | | |
|---|---|---|---|
| 5,261,910 A * | 11/1993 | Warden et al. ................ | 606/292 |
| 5,423,826 A | 6/1995 | Coates et al. | |
| 5,851,207 A | 12/1998 | Cesarone | |
| 6,342,057 B1 | 1/2002 | Brace et al. | |
| 6,379,364 B1 | 4/2002 | Brace et al. | |
| 6,436,103 B1 | 8/2002 | Suddaby | |
| 6,592,586 B1 * | 7/2003 | Michelson ...................... | 606/71 |
| 6,692,503 B2 | 2/2004 | Foley et al. | |
| 6,960,216 B2 | 11/2005 | Kolb et al. | |
| 7,081,119 B2 | 7/2006 | Stihl | |
| 7,357,804 B2 | 4/2008 | Binder, Jr. et al. | |
| 7,488,327 B2 | 2/2009 | Rathbun et al. | |
| 7,625,378 B2 | 12/2009 | Foley | |
| 7,731,721 B2 | 6/2010 | Rathbun et al. | |
| 7,763,029 B2 | 7/2010 | Rathbun et al. | |
| 7,963,980 B1 | 6/2011 | Freeman et al. | |
| 8,025,667 B2 | 9/2011 | Grant et al. | |
| 8,043,343 B2 | 10/2011 | Miller et al. | |
| 8,114,139 B2 * | 2/2012 | Sournac et al. ............... | 606/286 |
| 8,118,847 B2 * | 2/2012 | Wallenstein et al. ......... | 606/286 |
| 2005/0015093 A1 | 1/2005 | Suh et al. | |
| 2005/0137606 A1 | 6/2005 | Binder, Jr. et al. | |
| 2005/0283152 A1 * | 12/2005 | Lindemann et al. ........... | 606/61 |
| 2006/0189997 A1 | 8/2006 | Guenther et al. | |
| 2007/0093848 A1 | 4/2007 | Harris et al. | |
| 2008/0077152 A1 | 3/2008 | McClintock et al. | |
| 2008/0306550 A1 | 12/2008 | Matityahu | |
| 2009/0024132 A1 * | 1/2009 | Blain et al. ...................... | 606/96 |
| 2010/0185246 A1 | 7/2010 | Casteneda et al. | |

OTHER PUBLICATIONS

International Search Report and Written Opinion from corresponding PCT Application No. PCT/US2013/025152, Zavation LLC et al., issued Jun. 12, 2013, Authorized Officer In Ho Han, 14 pages.

* cited by examiner

*Primary Examiner* — David Bates
(74) *Attorney, Agent, or Firm* — Tarolli, Sundheim, Covell & Tummino LLP (57) ABSTRACT

The present invention relates to a surgical drill guide having an anchoring mechanism for locking the drill guide to a bone plate. The anchoring mechanism is adapted to be received through an opening of a bone plate and rotated to lock the drill guide to the bone plate. The anchoring mechanism can be rotated by a driver, which has a distal end key that fits into a corresponding socket of on the proximal portion of the anchoring mechanism. The present invention also relates to a kit including a bone plate, a driver, and the drill guide and a method for using the kit to perform surgery.

17 Claims, 12 Drawing Sheets

SURGICAL KIT FOR SPINAL SURGERY

TECHNICAL FIELD

The present invention relates to a surgical drill guide. The present invention also relates to a surgical kit including a bone plate, a driver, and a drill guide. The present invention also relates to systems and methods for spinal surgery.

BACKGROUND

Bone fixation systems for treating bone conditions are known. Surgical fixation plates may be used in a variety of orthopedic applications to stabilize, mend, align, or alter the compression of a patient's bones. A bone plate may be positioned over an injured area and secured to the bone, such as by bone screws.

A misalignment of the bone screws with the holes in the bone plate or improperly seated screws can cause tissue damage or an unstable connection of the plate to the bone. Thus, to ensure proper alignment of the bone screws with the holes in the bone plate, a drill guide is often used to assist the surgeon during the surgical procedure.

A separate plate holder may be used to place the plate at the target site. A drill guide may engage or abut the bone plate and generally includes a guide tube for receiving a drill bit therethrough. The drill guide may align with and/or lock to the screw holes of the bone plate to hold the drill guide steady while a hole is drilled into the bone. Alternatively, the drill guide may be connected to a different part of the bone plate so as not to interfere with the screw holes. If the drill guide is not configured to receive a screw therethrough, it may be removed from the bone plate after the hole has been drilled in the bone. However, since the plate may move before the bone screws are implanted, some drill guides are designed to also receive the screws therethrough.

US Patent Publication 2006/0189997 to Guenther et al. describes a drill guide for cervical plating that includes an alignment pin that can pass through the bone plate and into the bone. US Patent Publication 2008/0077152 to McClintock et al. describes a cervical drill guide that include a protrusion that engages the bone plate by a friction fit. U.S. Pat. No. 6,436,103 to Suddaby describes a drill guide including a plate attachment mechanism with arms to engage recesses of the bone plate. US Patent Publication 2007/0093848 describes a cervical drill guide that includes an extension member having a plurality of expandable fingers to engage a hole of the plate. U.S. Pat. No. 7,081,119 to Stihl describes a drill guide that can also be used as a plate holder, including an attachment mechanism and a locator pin. US Patent Publication 2009/0024132, U.S. Pat. No. 7,763,029, U.S. Pat. No. 7,488,327, U.S. Pat. No. 7,731,721, US Patent Publication 2005/0137606, U.S. Pat. No. 6,342,057, and U.S. Pat. No. 6,960,216 also describe drill guides with various alignment mechanisms to connect to bone plates. Other secure mechanisms for anchoring a drill guide to a bone plate are needed.

SUMMARY

The present invention provides systems and methods for positioning and implanting a bone plate to bone. An embodiment of the present invention provides a system and method for easily and securely locking a double-barrel drill guide to a bone plate by a rotatable anchoring member, which prevents lateral and rotational movement of the bone plate relative to the drill guide.

One embodiment of the present invention is a drill guide that includes a handle and a drill guide tube. The drill guide tube has an open proximal end, an open distal end, and a hollow lumen therebetween configured to receive a drill therethrough. The drill guide also has a distal planar portion having a proximal face, a distal face, and a hole therethrough. The drill guide further includes a rotatable anchoring member received within the hole of the distal planar portion. The anchoring member includes a proximal portion having a socket and distal portion having a flared distal end. The open distal end of the drill guide tube is configured to align with a screw hole of a bone plate such that a hole can be drilled into bone through the screw hole, wherein the distal face of the distal planar portion is configured to contact a front surface of the bone plate, and wherein the flared distal end of the anchoring member is configured to align with an opening in the bone plate and lock the drill guide to the bone plate upon rotation of the anchoring member.

A further embodiment of the present invention is a drill guide that includes a handle, a first drill guide tube and a second drill guide tube. The first drill guide tube has an open proximal end, an open distal end, and a hollow lumen therebetween configured to receive a drill therethrough. The second drill guide tube has an open proximal end, an open distal end, and a hollow lumen therebetween configured to receive a drill therethrough. The drill guide further includes a bridge portion connecting the distal end of the first drill guide tube and the distal end of the second drill guide tube. The bridge portion has a proximal face, a distal face, and a hole therethrough. The drill guide also includes a rotatable anchoring member received within the hole of the bridge portion. The rotatable anchoring member has a proximal portion having a socket and distal portion having a flared distal end. The distal ends of the drill guide tubes are configured to align with screw holes of a bone plate such that a hole can be drilled into bone through the screw holes. The distal face of the bridge portion is configured to contact a front surface of the bone plate and preferably conformally contact the front surface. The flared distal end of the anchoring member is configured to align with an opening in the bone plate and lock the drill guide to the bone plate upon rotation of the anchoring member.

Another embodiment of the present invention is a surgical kit that includes a bone plate and a drill guide. The bone plate includes a front surface and a back surface, and the back surface is adapted to contact a bone. The bone plate also includes a plurality of screw holes each configured to receive a screw therethrough and an opening for receiving the anchoring member of the drill guide. The drill guide has a handle, a first and second drill guide tube, a bridge portion, and a rotatable anchoring member. The first drill guide tube has an open proximal end, an open distal end, and a hollow lumen therebetween configured to receive a drill therethrough, and the second drill guide tube also has an open proximal end, an open distal end, and a hollow lumen therebetween configured to receive a drill therethrough. The bridge portion connects the distal end of the first drill guide tube and the distal end of the second drill guide tube. The bridge portion includes a proximal face, a distal face, and a hole therethrough. The rotatable anchoring member is received within the hole of the bridge portion The rotatable anchoring member includes a proximal portion having a socket and distal portion having a flared distal end. During use, the distal ends of the drill guide tubes align with screw holes of the bone plate, the distal face of the bridge portion contacts the front surface of the bone plate and the flared distal end of the anchoring member aligns with the opening in the bone plate and locks the drill guide to the bone plate upon rotation of the anchoring member.

A further embodiment of the present invention is a surgical kit including any one or more of a drill guide, a driver, a bone plate, and a plurality of screws. The driver includes a handle at a proximal end, and a key at a distal end. The bone plate includes a front surface and a back surface, wherein the back surface is adapted to contact a bone. The bone plate also includes a plurality of screw holes each configured to receive a screw therethrough. The bone plate also includes at least one screw lock. The screw locks have a socket to turn the screw lock between a locked position and an unlocked position. The key of the driver is sized to engage the socket of the screw locks. The screws have a head, which includes a socket, and a threaded shaft. Preferably, the key of the driver is also sized to engage the socket of the screws.

A further embodiment of the present invention is a method of implanting a cervical plate in a patient. The method includes using a surgical kit. The surgical kit includes a plate (preferably a cervical plate), a drill guide, and a driver. The cervical plate has a front surface and a back surface, wherein the back surface is adapted to contact a bone, preferably cervical vertebrae. The plate further includes a plurality of screw holes each configured to receive a screw therethrough and an opening for receiving an anchoring member of the drill guide. The kit also includes a drill guide having a handle, a first drill guide tube, and a second drill guide tube, a bridge portion, and a rotatable anchoring member. The first drill guide tube has an open proximal end, an open distal end, and a hollow lumen therebetween configured to receive a drill therethrough, and the second drill guide tube also has an open proximal end, an open distal end, and a hollow lumen therebetween configured to receive a drill therethrough. The bridge portion connects the distal end of the first drill guide tube and the distal end of the second drill guide tube. The bridge portion includes a proximal face, a distal face, and a hole therethrough. The drill guide also includes a rotatable anchoring member received within the hole of the bridge portion. The rotatable anchoring member has a proximal portion having a socket and distal portion having a flared distal end. The kit also includes a driver having a handle at a proximal end and a key at a distal end. The key is sized to engage the socket of the rotatable anchoring member of the drill guide. The method further includes the step of inserting the driver into the socket of the rotatable anchoring member. The method also includes the step of contacting the distal face of the bridge portion with the front surface of the cervical plate such that the distal ends of the drill guide tubes are aligned with the screw holes of the cervical plate and the flared distal end of the anchoring member is aligned with the opening in the cervical plate. The method also includes rotating the driver to lock the cervical plate to the drill guide, and placing the cervical plate at a target site in the patient while it is connected to the drill guide.

A further embodiment of the method of the present invention may further include the following steps: inserting a drill through the first drill guide tube; operating the drill to form a first hole in the bone; removing the drill from the first drill guide tube; inserting the driver having a first screw on the distal end thereof through the first drill guide tube; screwing the first screw into the first hole in the bone; and removing the driver from the first drill guide tube.

A further embodiment of the method of the present invention may further include the steps of inserting a drill through the second drill guide tube; operating the drill to form a second hole in the bone; and removing the drill from the second drill guide tube. The method may further include the steps of inserting the driver having a second screw on the distal end thereof through the second drill guide tube; screwing the second screw into the second hole in the bone; and removing the driver from the second drill guide tube. The method may further include the steps of inserting the driver into the socket of the rotatable anchoring member of the drill guide; rotating the driver to unlock the cervical plate from the drill guide; and removing the drill guide from the target site. The method may further include using the driver to turn screw locks to lock the first and second screws in place and removing the driver from the target site.

DETAILED DESCRIPTION

Figure 1:
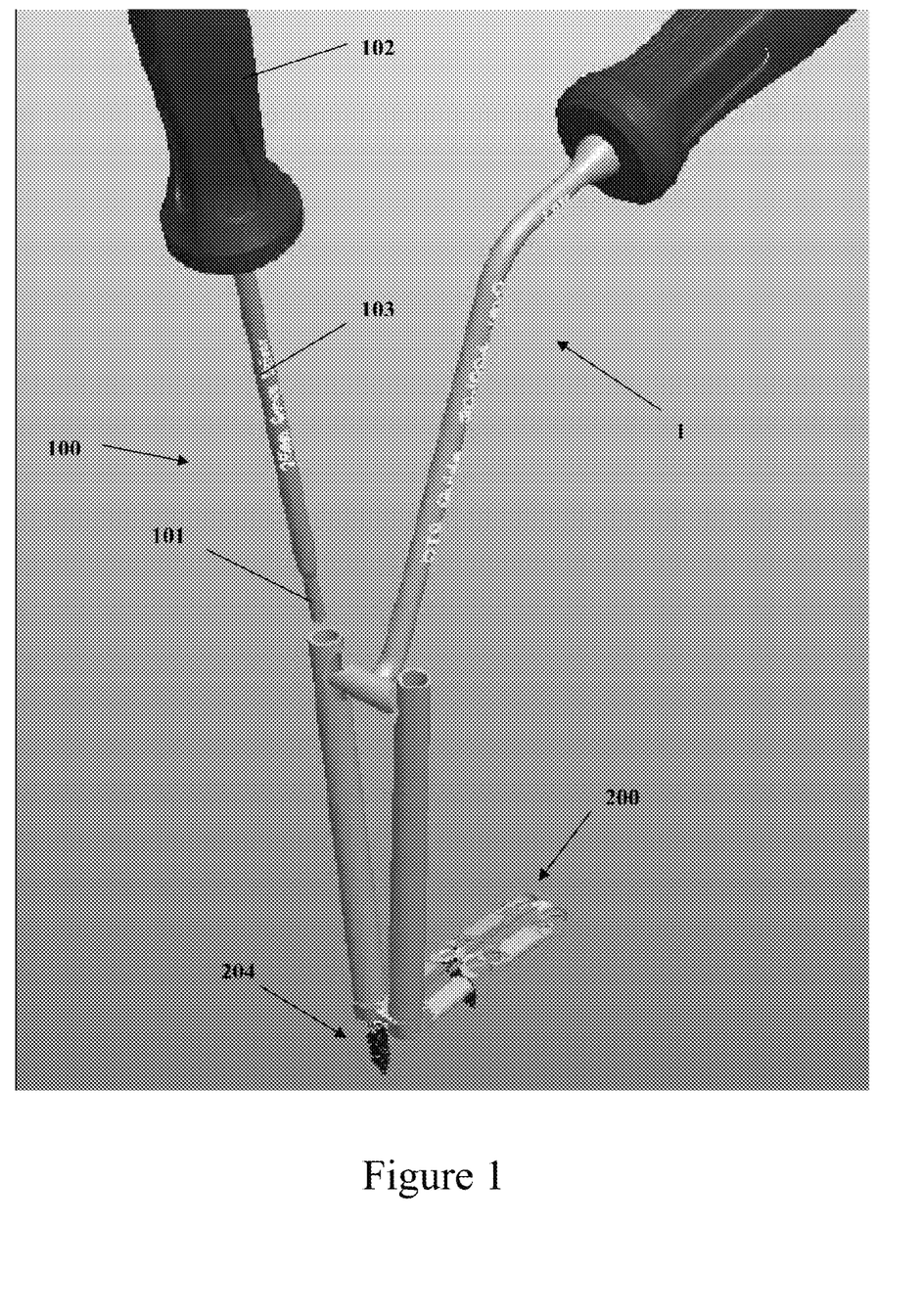
FIG. 1 shows a perspective view of an embodiment of a kit of the present invention including a driver, a drill guide, a bone plate, and screws.

FIG. 1 shows a perspective view of an embodiment of a kit of the present invention, which includes drill guide 1, driver 100, bone plate 200, and screws 204. In this Figure, drill guide 1 is shown connected to the bone plate 200, as will be described herein.

Figure 2:
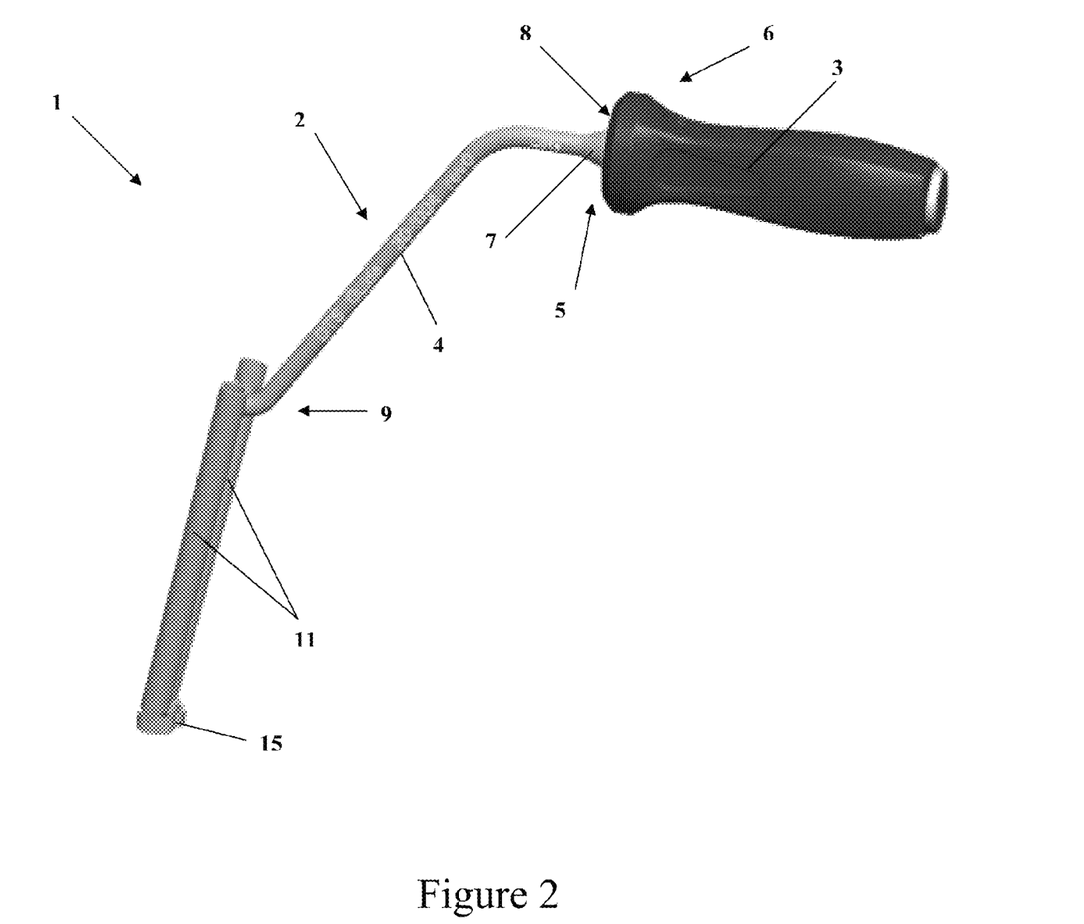
FIG. 2 shows a perspective view of an embodiment of a double-barrel drill guide of the present invention.
Figure 3:
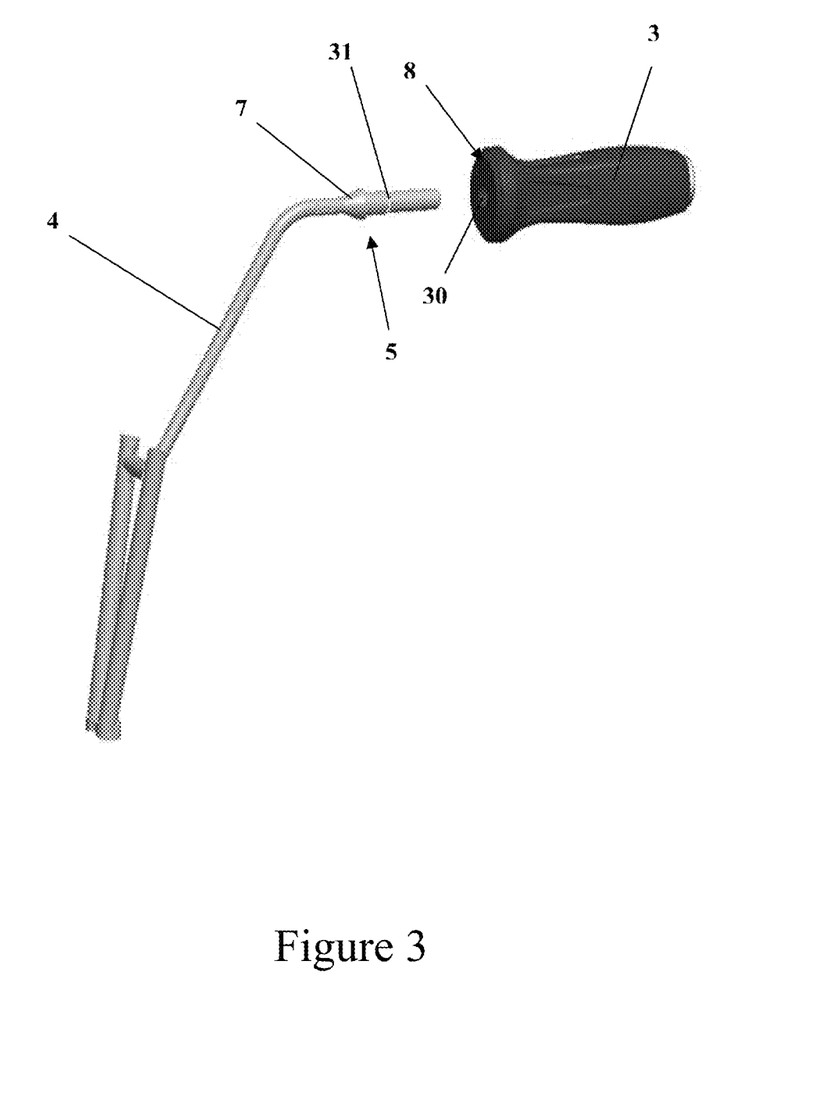
FIG. 3 shows an exploded view of an embodiment of a double-barrel drill guide of the present invention with a grip portion of a handle removed.

FIG. 2 shows a perspective view of drill guide 1. Drill guide 1 has a handle 2 at the proximal end thereof. The handle includes a grip portion 3 and a shaft portion 4. Shaft portion 4 includes a proximal section 5 and a distal section 9. Grip portion 3 is adapted to be held in a hand of an operator, such as a surgeon. The grip portion 3 may be rubberized and/or contoured to enhance the grip of the operator. The grip portion 3 may be removably attached to proximal section 5 of the shaft portion 4, such as by threading, to facilitate cleaning and sterilization. For example, a distal end 6 of the grip portion 3 may include a lumen 30 with threading on the inner surface thereof to cooperate with external threading 31 on an outer surface of proximal section 5 of shaft portion 4, as seen in FIG. 3. In one embodiment, an expanded neck portion 7 on proximal section 5 of the shaft portion 4 abuts a distal face 8 of the grip portion 3.

Figure 4:
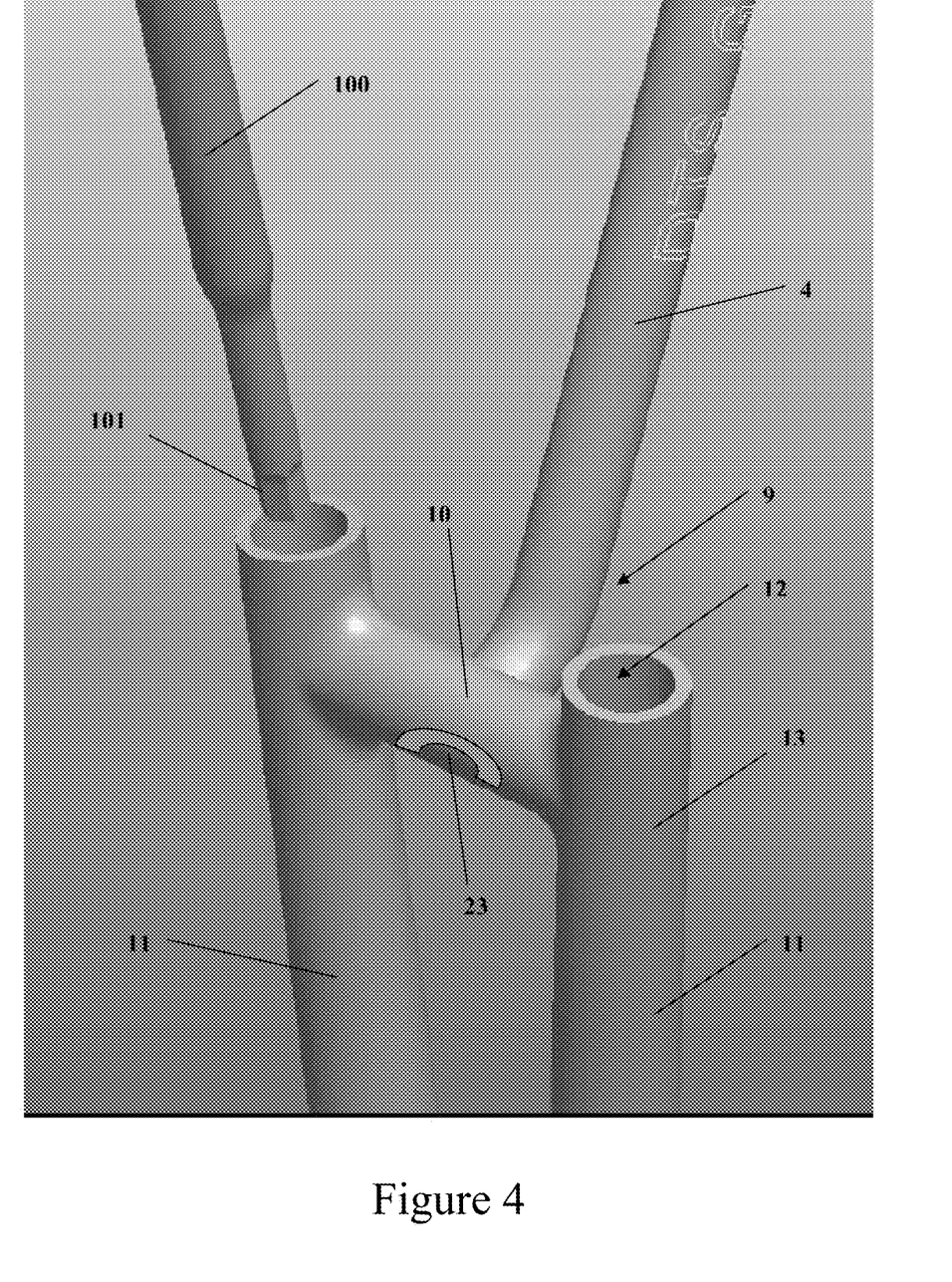
FIG. 4 shows an enlarged view of the proximal end of drill guide tubes of a drill guide and a driver of an embodiment of the present invention.
Figure 5:
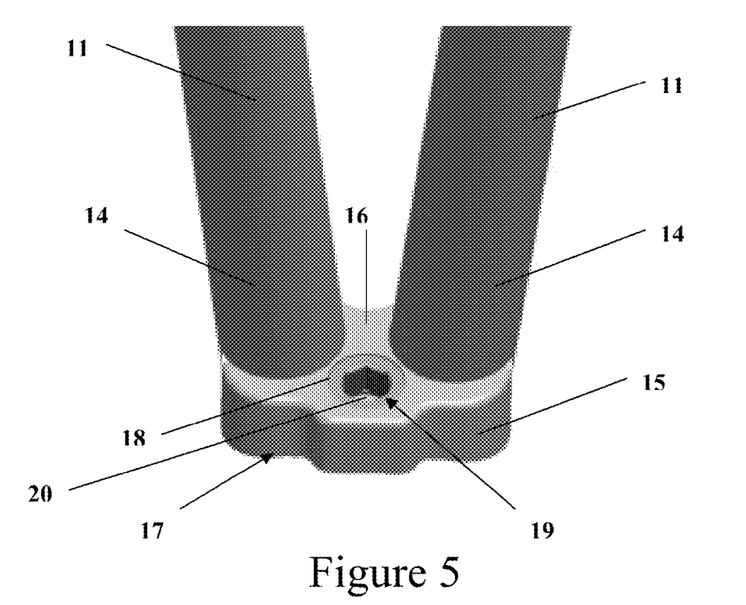
FIG. 5 shows an enlarged view of the distal end of a drill guide and an anchoring member according to an embodiment of the present invention.

With respect to FIG. 4, distal section 9 of shaft portion 4 ends at connecting portion 10, such as to form a T-shape configuration, although other configurations are possible. In certain embodiments, connecting portion 10 connects two drill guide tubes 11 to the shaft portion 4 of handle 2. Each drill guide tube 11 has lumen 12 therethrough with an open proximal end 13 and an open distal end 14 (an example of the distal end is shown in FIG. 5). In one embodiment, the drill guide tubes 11 are arranged such that the connecting portion 10 and the two drill guide tubes 11 form a triangle, as seen in FIG. 1. Thus, the drill guide tubes 11 are slanted with respect to each other such that a space between the proximal ends 13 is larger than a space between the distal ends 14 of drill guide tubes 11. Other configurations of the drill guide tubes in relation to the connecting portion are also possible. The drill guide tubes 11 are sized such that a distal end of a drill (not shown), such as the drill bit, can be received through the lumens 12 thereof. Additionally, the drill guide tubes 11 may be sized such that driver 100 can also be received through the lumen 12 thereof, as seen in FIG. 4. Drill guide tubes 11 may also be sized such that screws 204 can be received through the lumen 12 thereof. Connecting portion 10 may also include an indentation 23 on the outer surface thereof, as seen in FIG. 4. The shaft 103 of driver 100 (shown in FIG. 1) can rest in the indentation 23 when the driver 100 is used to rotate the rotatable anchoring mechanism 19, as will be described further herein. This allows the driver to align better with the drill guide.

Figure 6:
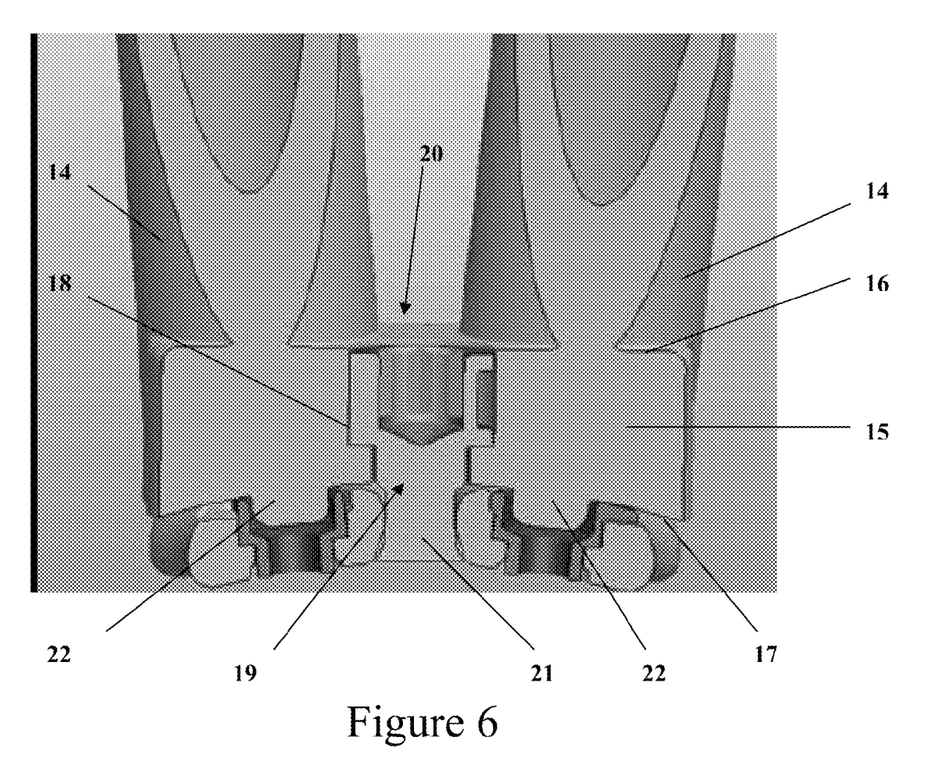
FIG. 6 shows a cross-sectional view of the distal end of the drill guide and anchoring member of FIG. 5.
Figure 7:
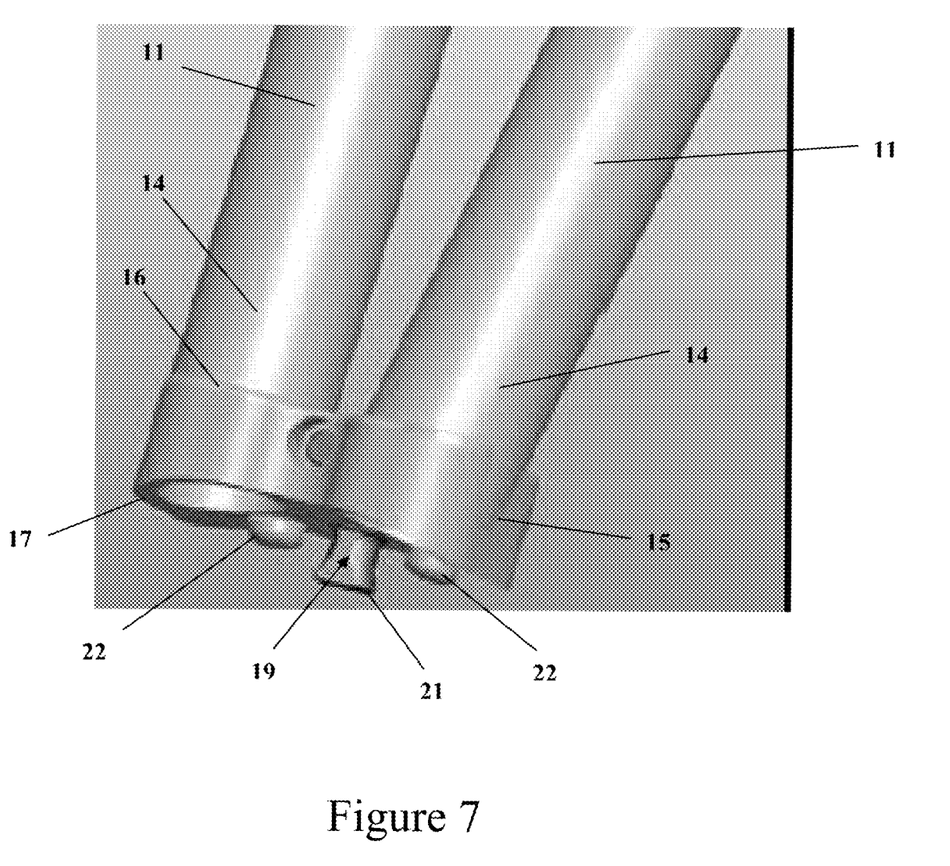
FIG. 7 shows an enlarged view of the distal end of a drill guide, an anchoring member, and alignment members according to an embodiment of the present invention.
Figure 12:
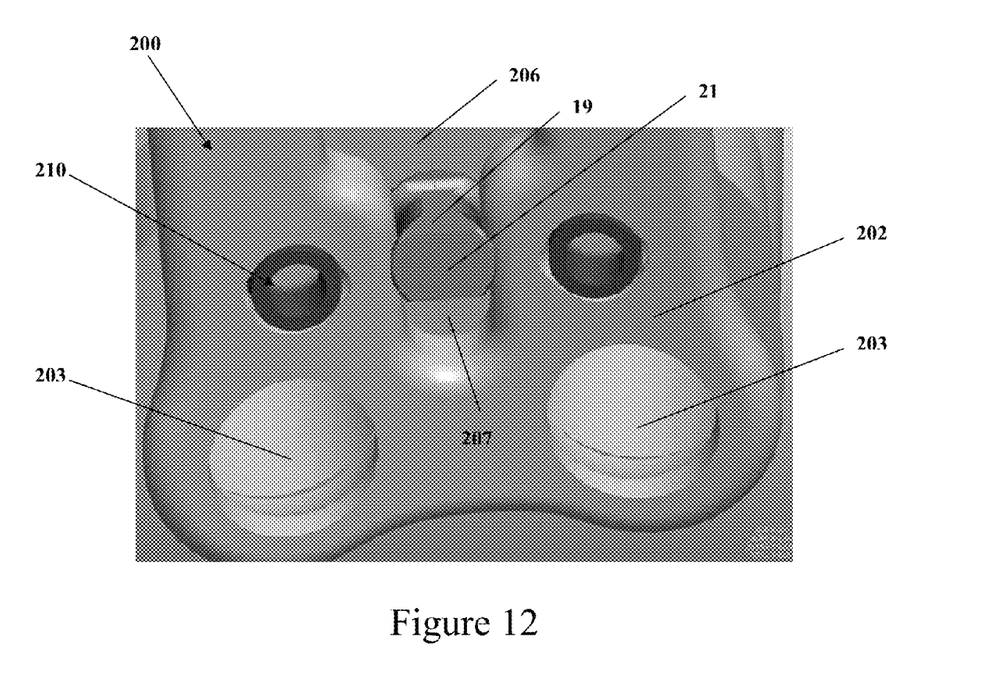
FIG. 12 shows an enlarged bottom view of a bone plate of the present invention, including the anchoring member in the locked position according to an embodiment of the present invention.
Figure 13:
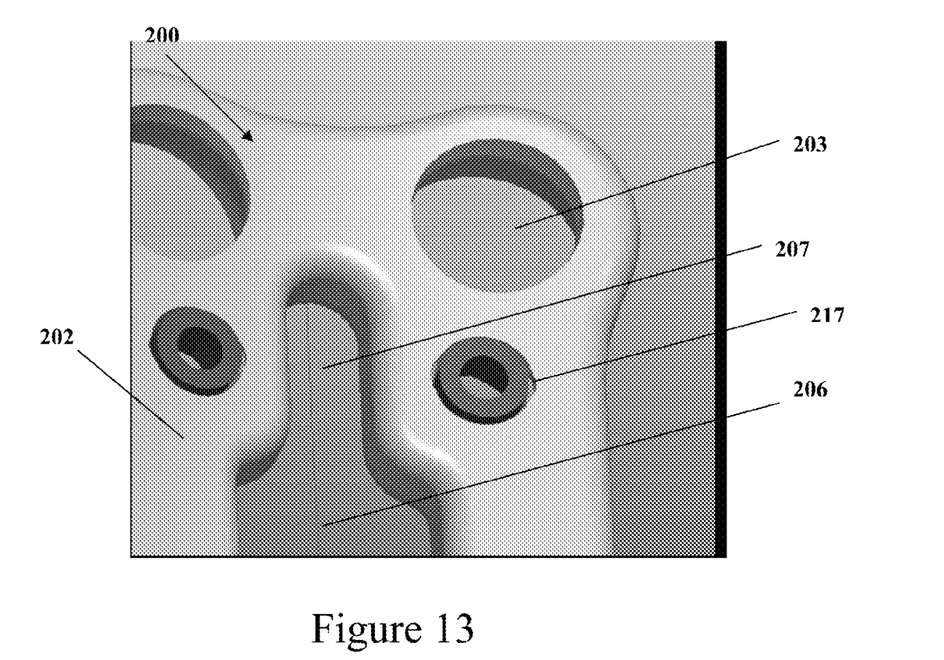
FIG. 13 shows an enlarged bottom view of an embodiment of a bone plate of the present invention without a drill guide attached thereto.

As seen in FIGS. 5-7, distal ends 14 of the two drill guide tubes 11 are connected together by a bridge portion 15 of drill guide 1. Bridge portion 15 is substantially planar and has a proximal face 16 and a distal face 17. Bridge portion 15 includes a hole 18 therethrough. An anchoring member 19 is rotatably mounted within hole 18. Anchoring member 19 is configured to anchor drill guide 1 to bone plate 200, as will be described further herein. Anchoring member 19 includes a proximal socket 20 (see FIG. 5) and flared distal end 21 (see FIG. 7). Socket 20 may be hex-shaped to receive driver 100 with a hex-shaped distal end key 101 (see FIG. 4). Of course, other complementary shapes are also possible. Flared distal end 21 may have an end face that is approximately oval-shaped, having two minor curved sides and two major straight sides, as seen in FIG. 12. Distal end 21 may have other suitable shapes as well. Bridge portion 15 may further include alignment members 22, as can best be seen in FIG. 7. Alignment members 22 may be projections on the distal face 17 of bridge portion 15 that are designed to fit into sockets 209 on screw locks 210 of a bone plate 200, as will be described further herein. Alignment members 22 may extend from the distal face 17 of the bridge portion 15 a distance A, and anchoring member 19 may extend from the distal face 17 of the bridge portion 15 a distance B, wherein A<B. Thus, in this embodiment, the anchoring member 19 is adapted to extend completely through the bone plate 200, while the alignment members 22 are only adapted to interface with the socket 209 and front surface 201 of the bone plate 200. Distal face 17 of bridge portion 15 may be concave, as seen in FIG. 7, so as to conform to a curved front surface 201 of a bone plate 200.

The shaft portion 4 of the handle 2, connecting portion 10, the two drill guide tubes 11, bridge portion 15, and alignment members 22 may all be formed as a unitary structure such that these components cannot be separated from each other if exposed to a normal amount of force without damaging the integrity of (i.e. breaking) the drill guide. Anchoring member 19 may be fixedly mounted in the hole 18 of bridge portion 15 during manufacturing. Anchoring member 19 may be rotatable between a locked position and an unlocked position, but preferably is not removable from the hole 18 of bridge portion 15.

In an exemplary embodiment, drill guide 1 is used together with driver 100 to implant bone plate 200 in a patient. In one embodiment, bone plate 200 may be a cervical plate, but could also be used for the lumbar region of the spine or for other orthopedic uses such as on the bones of the hand, the face or cranium to treat bone fractures or other conditions. The bone plate 200 may be a one-level, two-level, two-level, or four-level cervical plate for use in the spine. Alternatively, the bone plate may be a plate for use in any part of the body, such as the face, arms, legs, or vertebrae.

Figure 8:
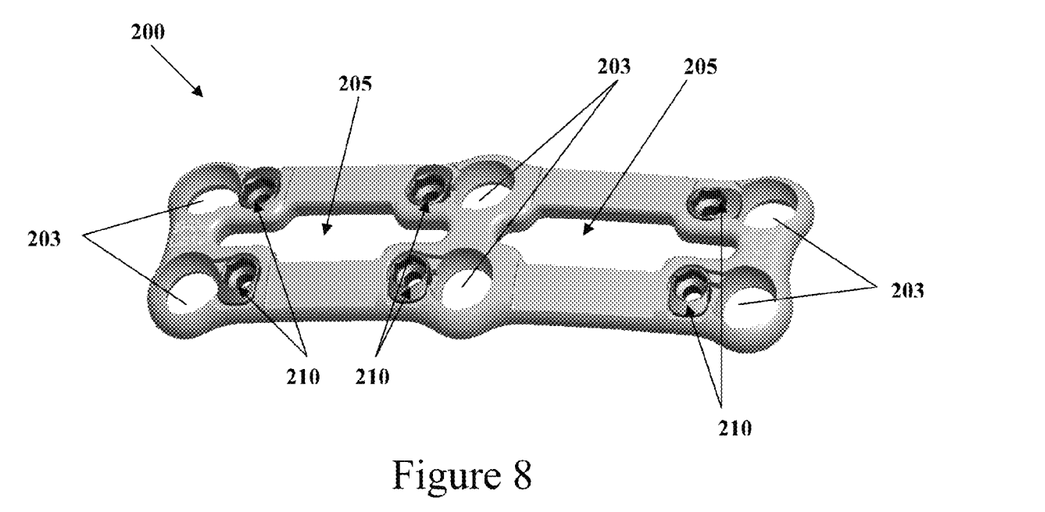
FIG. 8 shows a perspective view of an embodiment of a bone plate of the present invention.
Figure 9:
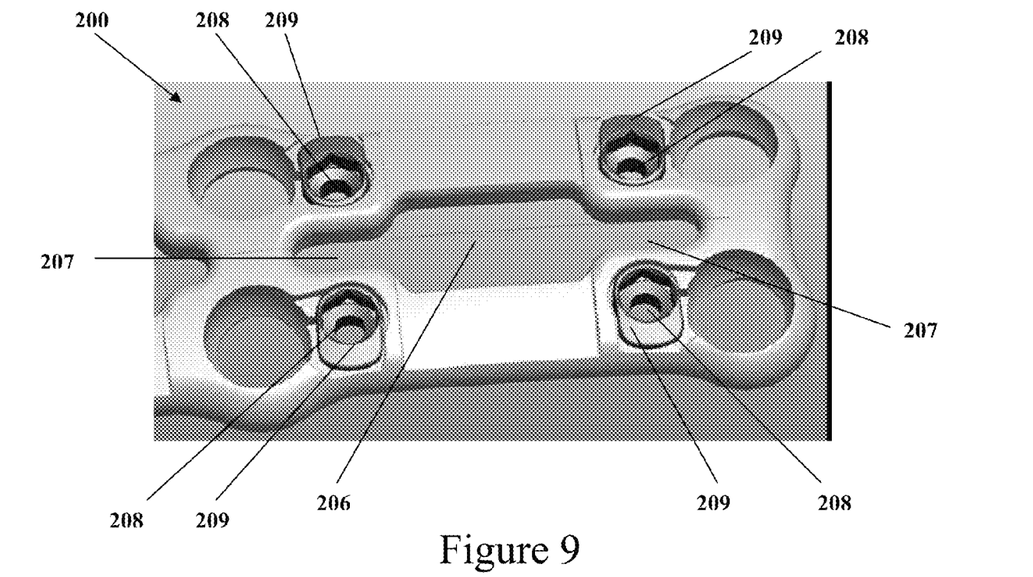
FIG. 9 shows an enlarged perspective view of the bone plate of FIG. 8.
Figure 10:
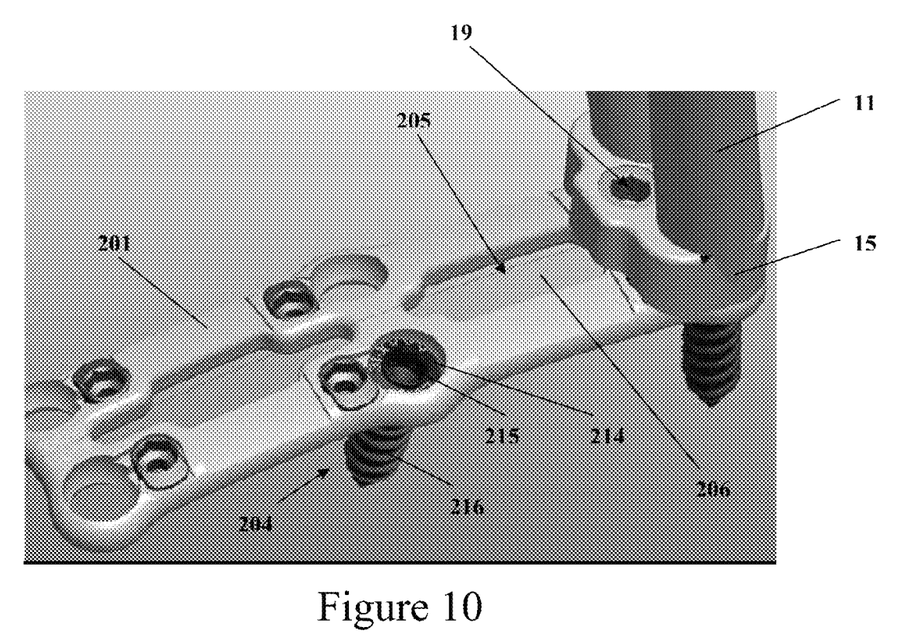
FIG. 10 shows a perspective view of a bone plate and drill guide according to an embodiment of the present invention, with the drill guide connected thereto, including screws.
Figure 11:
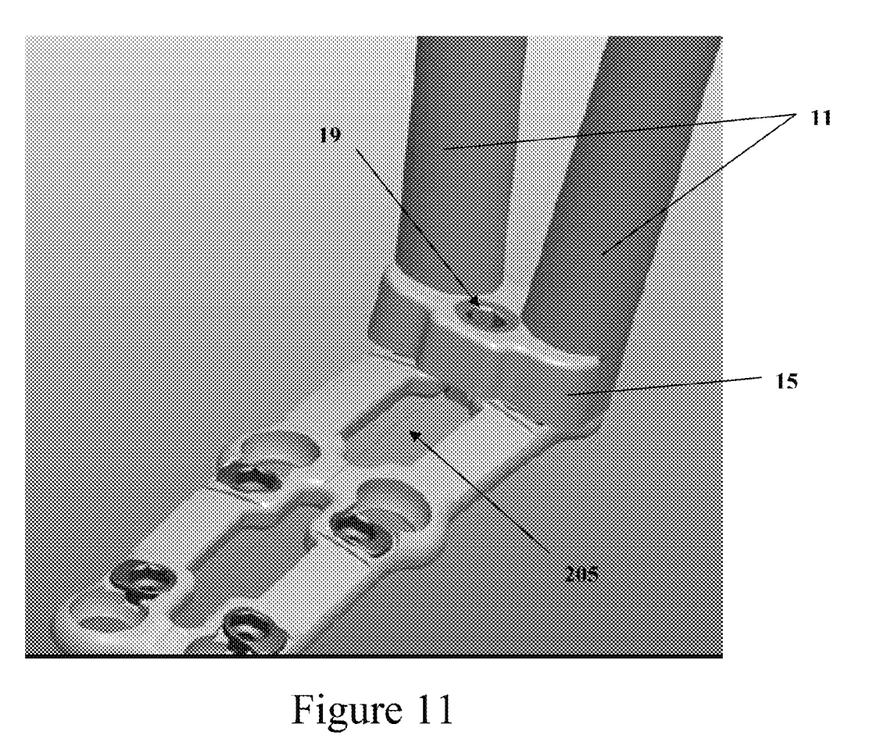
FIG. 11 shows the perspective view of the bone plate and drill guide of the present invention of FIG. 9, without the screws.

FIGS. 8-14 show an exemplary bone plate 200, which includes a front surface 201 and a back surface 202. Front surface 201 is an accessible surface that is adapted to contact the drill guide 1 and back surface 202 is adapted to contact a bone upon implantation. Bone plate 200 includes a plurality of screw holes 203 for receiving bone screws 204 therethrough. In the embodiment shown in FIGS. 8-14, a two-level cervical plate 200 includes six screw holes 203 but as stated above, the cervical plate can include more or less screw holes depending on how many levels of the cervical region the bone plate is to be attached to. As seen in FIG. 10, bone screws 204 include head 214 having socket 215 and threaded shaft 216. Socket 215 may be hex-shaped to receive driver 100 with a hex-shaped distal end key 101, but could include other shapes complementary with the distal end key of the driver.

Figure 14:
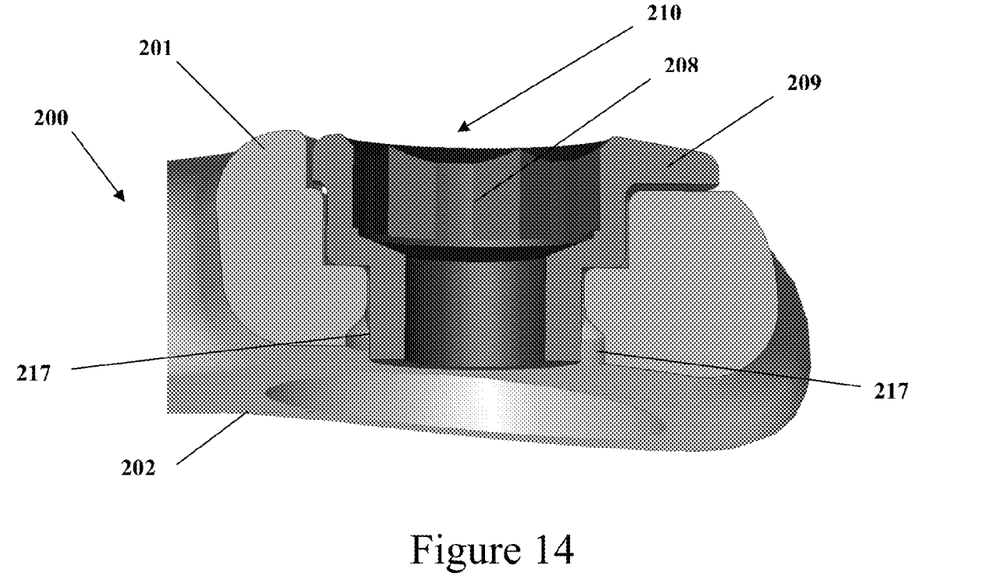
FIG. 14 shows a cross-sectional view of a screw lock in a bone plate according to an embodiment of the present invention.
Figure 15:
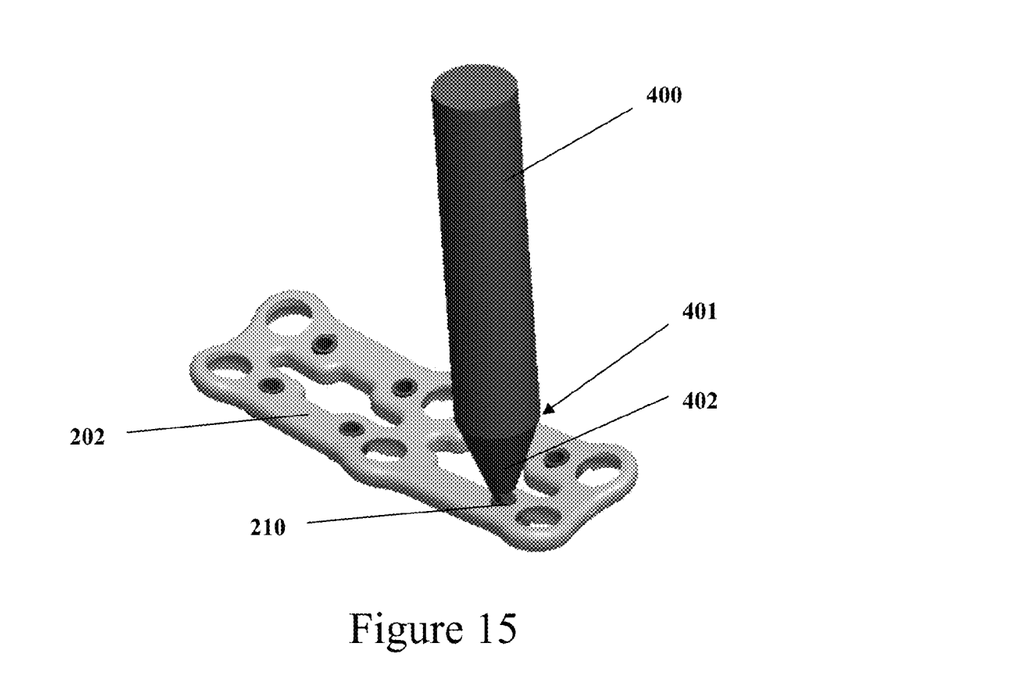
FIGS. 15-17 show a rivet tool for assembling a screw lock in a bone plate according to an embodiment of the present invention.
Figure 16:
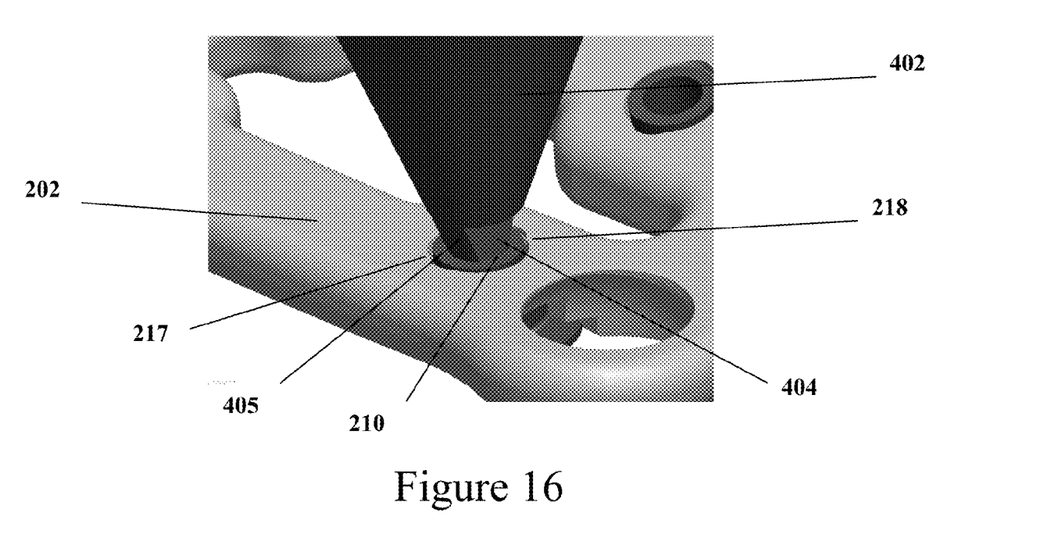

Bone plate 200 may also include screw locks 210 for preventing backing-out of the screws 204 after they are inserted into the bone. In the embodiment shown in FIGS. 8-14, bone plate 200 includes six screw locks 210, one for each screw hole 203. Alternatively, the plate may be designed such that one screw lock is configured to lock the head of more than one screw. Screw locks 210 have a socket 208 and a tab 209, as best seen in FIG. 14. Referring to FIGS. 15 and 16, in certain embodiments, a hole 218 in the bone plate 200 for receiving the screw locks 210 includes cut-out area 217 to enable the material from the screw lock 210 to deform into this cut-out area 217 when the screw lock 210 is in the locked position. Socket 208 of the screw lock may be hex-shaped to receive driver 100 with a hex-shaped distal end key 101. Of course the socket could include another shape complementary with the distal end key of the driver. Driver 100 can be inserted into socket 208 to turn the screw lock 210 from an unlocked position to a locked position. In a locked position, tab 209 covers a portion of head 214 of screw 204 to prevent the screw 204 from backing out.

Bone plate 200 also includes at least one opening 205 in a central portion thereof. Preferably openings 205 are provided between each set of screw holes 203. As seen in FIG. 8, one embodiment of bone plate 200 includes two openings 205. Openings 205 may be elongated such that an operator can view the surgical area therethrough. Openings 205 may include a central window area 206 and at least one end window area 207. Preferably central window area 206 is wider than end window areas 207, as seen in FIG. 9. The narrower end window area 207 can extend between the screw locks 210 and may also extend partially between the screw holes 203. Of course, other configurations of the opening are also possible. The end window area 207 is shaped and sized to receive flared distal end 21 of anchoring member 19 of drill guide 1, as seen in FIG. 12, in order to lock the drill guide 1 to the bone plate 200.

Drill guide 1 can be anchored to the bone plate 200 to prevent movement of the drill guide tubes 11 relative to the screw holes 203, such as while a hole is being drilled into the bone. In a first position, distal face 17 of bridge portion 15 is preferably in conformal contact with front surface 201 of bone plate 200, and the two drill guide tubes 11 are aligned with two adjacent screw holes 203. In this position, the alignment members 22 may also be aligned with sockets 208 of screw locks 210. Alignment members 22 may contact the sockets 208 with a friction fit, or alternatively alignment members 22 may have a circumference that is smaller than the sockets 208 and may fit loosely therein. In this first position, anchoring member 19, including flared distal end 21, is received through end window area 207 of bone plate 200 in an unlocked position.

In order to lock drill guide 1 to plate 200, anchoring member 19 is rotated from the unlocked position to a locked position. In the locked position, flared distal end 21 contacts the back surface 202 of the bone plate 200 to anchor the drill guide 1 thereto. The anchoring member 19 may be rotated, such as by driver 100, from an unlocked position to a locked position. The anchoring member may be rotated, for example, 90 degrees clockwise, to move from the unlocked position to the locked position, as seen in FIGS. 6 and 12. To remove the drill guide 1 from the plate 200, the anchoring member 19 is rotated, for example, 90 degrees counterclockwise, from the locked position to the unlocked position. A stop (not shown) within the bridge portion 15 may prevent the anchoring member 19 from moving except between the locked position and the unlocked position. Of course, other ways of rotating the anchoring member to lock and unlock the drill guide to the bone plate are possible.

In order to perform an exemplary surgical procedure, once the drill guide 1 is anchored to the plate 200, a drill (not shown) can be inserted into the lumen 12 of a first drill guide tube 11 and a hole can be drilled in the bone. Then, the drill can be removed from the first drill guide tube 11 and a screw 204 and driver 100 can be inserted into the first drill guide tube 11 to anchor the bone plate 200 to the bone. These steps may then be repeated with the second drill guide tube 11 without the drill guide 1 having to be moved from the first location. After holes have been drilled through both the first and second drill guide tubes 11, and screws 204 have been inserted into the bone through the first and second drill guide tubes 11, the drill guide 1 can then be moved to a second location. In order to move the drill guide 1, the anchoring member 19 can be rotated to the unlocked position, such as by using driver 100, and the drill guide 1 can be unlocked from the bone plate 200. The drill guide 1 can then be anchored to a second location on the bone plate 200. In one embodiment, the driver 100 can also be used to turn the screw locks 210 from an unlocked position to a locked position after the screws 204 are placed in the bone through the bone plate 200.

Driver 100 can include handle 102 at a proximal end, key 101 at a distal end, and a shaft 103 therebetween. Distal end key 101 is shaped to engage a socket, such as socket 20 of anchoring member 19, socket 215 of screw 204, and/or socket 208 of screw lock 210. In a preferred embodiment, the key 101 of driver 100 is shaped and sized to engage all of the sockets of the kit: socket 20, socket 215, and socket 208. Key 101 may be hex-shaped, and sockets 20, 215, and 208 may be correspondingly hex-shaped. Other corresponding shapes for the key 101 and the sockets 20, 215 and 208 are of course also possible. Shaft 103 is preferably sized and shaped to fit through the lumen 12 of drill guide tubes 11.

Figure 17:
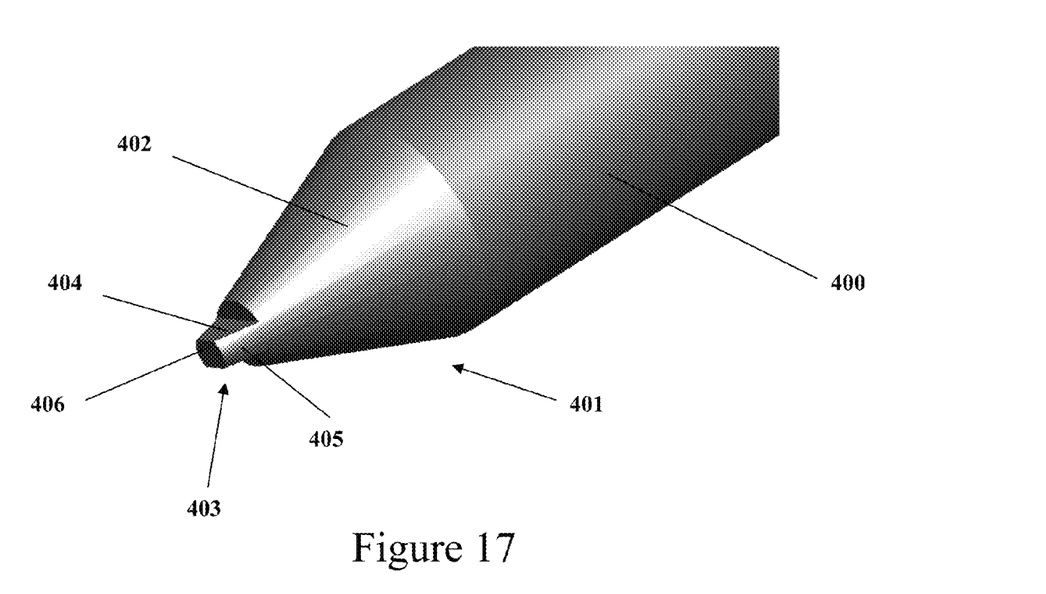

In order to mount screw locks 210 in bone plate 200, a rivet tool 400 can be used, as seen in FIGS. 15-17. In certain embodiments, during manufacturing, screw lock 210 is inserted in hole 218 in plate 200. Then, as seen in FIGS. 15 and 16, a distal end 401 of tool 400 is inserted into the screw lock 210 from the bottom surface 202 of the plate 200 while the screw lock 210 is in the locked position. FIG. 17 shows distal end 401 of tool 400 having a proximal cone-shaped portion 402 and a stepped distalmost end 403. Distalmost end 403 has two side portions 404 with material removed therefrom to create an oval-shaped distal end face 406. When distalmost end 403 is inserted into the bottom of screw lock 210, and pressure is applied thereto, the larger side portions 405 if tool 400 push the material of the screw lock 210 into the cut-out areas 217 of hole 218 in bone plate 200 to permanently anchor the screw lock 210 therein.

Since the screw lock is mounted in the hole 218 while in the locked position, there is a tactile feel for the user when the screw lock 210 is rotated from an unlocked position to a final locked position during use. This is due to the material that was deformed into the cut-out areas 217 of hole 218 during manufacturing expanding into the cut-out areas 217 when the screw lock reached the final locked position. Thus, a greater force is necessary for the user to rotate the screw lock 210 from the locked position to the unlocked position, providing a more secure lock for the screws 204.

Although the exemplary embodiment illustrates a drill guide having two drill tubes, or a double-barrel drill guide, the invention may alternatively include a single-barrel drill guide having only one drill guide tube.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A surgical kit comprising:
    a driver comprising:
        a handle at a proximal end, and a key at a distal end;
    a bone plate comprising:
        a front surface and a back surface, the back surface adapted to contact a bone and having walls defining at least one hole, the at least one hole defining a cut out area;
        an opening for receiving a rotatable anchoring member therein;
        a plurality of screw holes each configured to receive a screw therethrough;
        at least one screw lock comprising a socket to turn the at least one screw lock between a locked position and an unlocked position, wherein the key of the driver is sized to engage the socket of the screw lock, wherein the at least one screw lock is compressed by the walls of the hole when the at least one screw lock it in the unlocked position and it is configured to not expand into the cut out area in the unlocked position and decompresses into the cut out area when the at least one screw lock is in the locked position; and a plurality of screws having a head and a threaded shaft, each screw comprising a socket on the head thereof, wherein the key of the driver is sized to engage the socket of the screws; and a drill guide comprising the rotatable anchoring member comprising a proximal portion having a socket and distal portion having a flared distal end.

2. The surgical kit of claim 1, wherein the socket of each of the plurality of screws, and the socket of the at least one screw lock are all substantially identically sized and shaped to receive the key of the driver.

3. The surgical kit of claim 1, wherein the bone plate is a cervical plate.

4. The surgical kit of claim 1, wherein the opening in the bone plate for receiving the anchoring member is located between two screw locks of the at least one screw lock.

5. The surgical kit of claim 1, wherein the key of the driver is sized to engage the socket of the rotatable anchoring member.

6. The surgical kit of claim 5, wherein the socket on the proximal portion of the anchoring member is hex-shaped, and the key at the distal end of the driver is reciprocally hex-shaped.

7. The surgical kit of claim 1, wherein the socket of the anchoring member, the socket of each of the plurality of screws, and the socket of the at least one screw lock are all substantially identically sized and shaped to receive the key of the driver.

8. The drill guide of claim 1, wherein the anchoring member has an unlocked position and a locked position,
wherein in the unlocked position, the flared distal end fits through the opening of the bone plate, and
wherein in the locked position, the flared distal end is rotated such that a portion of the flared distal end contacts the back surface of the bone plate.

9. The drill guide of claim 1, wherein the flared distal end of the anchoring member has an approximately oval-shaped end face, having two minor curved sides and two major straight sides.

10. The drill guide of claim 1, further comprising:
a first alignment member configured to align with a first screw lock of the at least one screw lock on the bone plate; and
a second alignment member configured to align with a second screw lock of the at least one screw lock on the bone plate.

11. The surgical kit of claim 1, wherein the drill guide further comprises:
a handle;
a drill guide tube having an open proximal end, an open distal end, and a hollow lumen therebetween configured to receive a drill therethrough;
a distal planar portion comprising: a proximal face, a distal face, and a hole therethrough; and
the rotatable anchoring member received within the hole of the distal planar portion,
wherein the open distal end of the drill guide tube is configured to align with a screw hole of the bone plate such that a hole can be drilled into bone through the screw hole,
wherein the distal face of the distal planar portion is configured to contact the front surface of the bone plate, and
wherein the flared distal end of the anchoring member is configured to align with the opening in the bone plate and lock the drill guide to the bone plate upon rotation of the anchoring member.

12. The surgical kit of claim 1, wherein the drill guide further comprises:
a handle;
a first drill guide tube having an open proximal end, an open distal end, and a hollow lumen therebetween configured to receive a drill therethrough;
a second drill guide tube having an open proximal end, an open distal end, and a hollow lumen therebetween configured to receive a drill therethrough;
a bridge portion connecting the distal end of the first drill guide tube and the distal end of the second drill guide tube, the bridge portion comprising: a proximal face, a distal face, and a hole therethrough; and
the rotatable anchoring member received within the hole of the bridge portion,
wherein the distal ends of the drill guide tubes are configured to align with screw holes of the bone plate such that a hole can be drilled into bone through the screw holes,
wherein the distal face of the bridge portion is configured to contact the front surface of the bone plate, and
wherein the flared distal end of the anchoring member is configured to align with the opening in the bone plate and lock the drill guide to the bone plate upon rotation of the anchoring member.

13. The drill guide of claim 12, further comprising:
a first alignment member configured to align with a first screw lock of the at least one screw lock on the bone plate; and
a second alignment member configured to align with a second screw lock of the at least one screw lock on the bone plate.

14. The drill guide of claim 13, wherein the first alignment member is a first projection on the distal face of the bridge portion, and the second alignment member is a second projection on the distal face of the bridge portion.

15. The drill guide of claim 14, wherein the distal portion of the anchoring member extends from the distal face of the bridge portion a first distance, the first and second projections extend from the distal face of the bridge portion a second distance, and the first distance is greater than the second distance.

16. The drill guide of claim 12, wherein the first and second drill guide tubes are also configured to receive the driver.

17. The drill guide of claim 12, wherein the distal face of the bridge portion is concave and conforms to the front surface of the bone plate.

* * * * *